US009810606B2

(12) United States Patent
Houghton et al.

(10) Patent No.: US 9,810,606 B2
(45) Date of Patent: Nov. 7, 2017

(54) METHODS AND DEVICES FOR VAPOR SAMPLING

(71) Applicant: SRC, Inc., North Syracuse, NY (US)

(72) Inventors: Stephen R. Houghton, Tully, NY (US); Marc P. Roberts, Alexandria, VA (US); Robert M. Cannon, Clay, NY (US)

(73) Assignee: SRC, Inc., North Syracuse, NY (US)

( * ) Notice: Subject to any disclaimer, the term of this patent is extended or adjusted under 35 U.S.C. 154(b) by 46 days.

(21) Appl. No.: 15/012,248

(22) Filed: Feb. 1, 2016

(65) Prior Publication Data
US 2017/0219464 A1    Aug. 3, 2017

(51) Int. Cl.
*G01N 1/00* (2006.01)
*G01N 1/22* (2006.01)
*G01N 21/65* (2006.01)

(52) U.S. Cl.
CPC ........... *G01N 1/2208* (2013.01); *G01N 21/65* (2013.01)

(58) Field of Classification Search
CPC ........... G01N 15/0255; G01N 15/0612; G01N 2001/2223; G01N 2015/0088; G01N 2015/0261; G01N 23/12; G01N 15/0205; G01N 15/042; G01N 15/0618;
(Continued)

(56) References Cited

U.S. PATENT DOCUMENTS

| 4,473,296 | A | * | 9/1984 | Shofner | G01N 21/53 356/336 |
| 4,902,318 | A | * | 2/1990 | Stevens | G01N 1/2208 55/320 |
| 4,961,916 | A | | 10/1990 | Lesage et al. | |

(Continued)

FOREIGN PATENT DOCUMENTS

| CN | 103063623 | 4/2013 |
| EP | 0352126 | 1/1990 |

(Continued)

OTHER PUBLICATIONS

Taewon, H., et al., "Aerosol Deposition on Electroformed Wire Screens", Aerosol Science and Technology, vol. 43:2, p. 112-119, Oct. 19, 2015, DOI: 10.1080/02786820802499050.
(Continued)

*Primary Examiner* — Michael P Stafira
(74) *Attorney, Agent, or Firm* — Bond Schoeneck & King, PLLC; George McGuire; Blaine Bettinger

(57) ABSTRACT

Various embodiments and implementations herein are directed to an aerosol and vapor sampling device that has a nozzle capable of focusing/concentrating the sampled particles by accelerating them in a narrow jet and driving the particles into an impaction well containing a collection substrate. The aerosolized particles, aerosolized droplets, and chemical vapors are retained by using a porous collection substrate, having substantial depth and mounted on a porous backing, such as a screen. This configuration allows a minor air flow through the collection substrate. This minor flow allows a well impactor to retain intercepted aerosolized particles. It also improves the inlet's ability to collect and retain chemical vapors or liquid aerosol droplets that are partially filtered and captured in the substrate's matrix.

14 Claims, 4 Drawing Sheets

(58) Field of Classification Search
CPC .. G01N 15/0625; G01N 15/10; G01N 1/2202; G01N 1/2208
See application file for complete search history.

(56) References Cited

U.S. PATENT DOCUMENTS

| | | | |
|---|---|---|---|
| 5,317,930 | A | 6/1994 | Wedding |
| 5,702,506 | A | 12/1997 | Shih et al. |
| 2002/0062702 | A1 | 5/2002 | Bradley |
| 2004/0232052 | A1 | 11/2004 | Call et al. |
| 2005/0247868 | A1* | 11/2005 | Call ............ G01N 15/0255 250/282 |
| 2009/0317916 | A1 | 12/2009 | Ewing et al. |
| 2014/0262837 | A1* | 9/2014 | Sidheswaran ...... G01N 33/0014 205/785.5 |
| 2014/0286836 | A1 | 9/2014 | Clavaguera et al. |
| 2016/0109349 | A1* | 4/2016 | Volckens ............ G01N 1/2202 356/318 |

FOREIGN PATENT DOCUMENTS

| | | |
|---|---|---|
| EP | 1041377 | 4/2000 |
| WO | 9306910 | 4/1993 |
| WO | 03081212 | 10/2003 |

OTHER PUBLICATIONS

Ewing, K.J., et al., "Sampler for Collection and Analysis of Low Vapor Pressure Chemical (LVPC) Particulates/ Aerosols", American Chemical Society, Article 85, 2013, pp. 9508-9513.

Abdel-Salam BSc, M., and Dennis, PhD., John H., "Review of Aerosol Sampling Methods and Introduction of a New Low Cost Aerosol Sampler", Aerosol Sampler, Department of Environmental Science, University of Bradford, Bradford UK BD7 1DP., pp. 1-14.

International Search Report and Written Opinion Form PCT/ISA/220, International Application No. PCT/US2017/012790, pp. 1-11, dated Apr. 5, 2017.

\* cited by examiner

```
       502 ─┐    Providing an aerosol sampling device having a collection well with a porous
                                            backing

↓

504 ─┐    Inputting a gas sample to the opening of a particle focusing nozzle of the
                                       aerosol sampling device

↓

506 ─┐    Analyzing a plurality of particulates captured in the porous collection
                                            substrate
```

FIG. 4

METHODS AND DEVICES FOR VAPOR SAMPLING

BACKGROUND

The present disclosure is directed generally to an aerosol particulate capture mechanism, and more particularly to an aerosol particulate capture mechanism that permits the flow of gas through the collection substrate.

Aerosol particle capture mechanisms are generally described by the physical interaction of a particle with a collection surface. Examples of some interactions are diffusion, interception, impaction, inertial impaction, gravitation settling, and electrostatic attraction among others. These interactions are dependent on the size, shape, and charge of the particles sampled and the physical characteristics of the respective collection surface. Some aerosol samplers sort particulate matter by aerodynamic diameters of a certain size while others attempt to capture as much material as possible regardless of particle size.

Previously, filtration devices employing the use of a surface filter can effectively filter aerosolized particles from sampled air, but particles are collected on a large surface decreasing the effective surface concentration and increasing particle bounce while generating a high pressure drop across the filtration media. To prevent particle bounce, some filters have an integrated electret filter which can reduce the need for high face velocities and prevent destruction of viable microorganisms by impaction while retaining by electrostatic charge effects. In addition, filtration devices have historically had inherently high pressure drops across the collection membranes, particularly for filters that have porosity and depth. Often times a high vacuum sampling pump is required to utilize fiber depth filters.

As mentioned, one of the main deficiencies of many types of aerosol samplers is particle bounce. This deficiency can result in reduced particle collection efficiencies; particularly for particles that exhibit repulsive verses attractive forces with the collection surface. One method to overcome this force is to accelerate the particles at a high velocity and drive them into a tacky/oily surface or to impact or entrap them into a liquid impinger. These methods are not conducive to in-situ analysis during collection, require post-sample collection clean up and processing, and generally do not concentrate all the particles sampled in a small surface area. Instead, the particles are eluted from the filter, causing dilution, and require manual concentration following collection.

In addition, impaction wells are often designed to comply with dimensions that favor collection of particles of a certain size. All impactors currently in the art have solid support under the collection material. This means there is no air flow through the collection media and its depth and filamented fibers are the primary entrapment mechanism. In addition, many depth filters such as, but not limited to, borosilicate glass, quartz, other forms of silicon dioxide, ceramic, metallic, and polymer based filters have naturally occurring electrets as opposed to induced electrets to help with particle retention.

Accordingly, there is a need in the art for an aerosol sampling device that can sample particulates while minimizing bounce and that does not rely solely on the depth of collection media, liquid entrapment, electrolytic effects, or methods requiring high vacuum to retain particulates.

SUMMARY

The present disclosure is directed to inventive methods and systems for an aerosol sampling device that can sample particulates while minimizing bounce and does not rely on the depth of the collection media to retain the particulates. Various embodiments and implementations herein are directed to a medium velocity aerosol sampling device that has a nozzle capable of focusing/concentrating the sampled particles by accelerating them in a narrow jet and driving the particles into an impaction well containing a collection substrate. The aerosolized particles or droplets are retained by using a porous collection substrate, having substantial depth and mounted on a porous backing, such as a screen. This configuration allows a minor air flow through the collection substrate. This minor flow allows a well impactor to retain intercepted aerosolized particles. It also improves the inlet's ability to collect and retain chemical vapors or liquid aerosol droplets that are partially filtered and captured in the substrate's matrix.

In accordance with an aspect, an aerosol sampling device is provided. The aerosol sampling device includes: a particle focusing nozzle comprising an elutriator column having an opening at a first end and an accelerator jet outlet at a second end opposite said first end, where the particle focusing nozzle is configured to admit a gas-aerosol sample at the opening and to vent the gas-aerosol sample at the jet outlet; a collection well, positioned to receive the gas-aerosol sample from the jet outlet, and comprising a backing and a sidewall, where at least a portion of the backing is porous such that at least part of the received gas-aerosol sample may flow through the porous portion of the backing.

According to an embodiment, the device further comprises a porous collection substrate in a covering relationship with the porous backing such that at least a portion of the gas-aerosol sample passes through the porous collection substrate, trapping a portion of the aerosols and chemical vapors of the gas-aerosol sample within the porous collection substrate.

According to an embodiment, the device further comprises a sampling chamber, where the sample has a first end having an opening for receiving the second end of the of particle focusing nozzle, and a second end having an outlet to vent the gas received from the particle focusing nozzle.

According to an embodiment, the collection well is suspended in the sampling chamber by a plurality of supports, wherein the supports are spaced to allow at least some of the gas received from the particle focusing nozzle to pass between the supports and to exit the sampling chamber via the second end.

According to an embodiment, the porous portion of the backing is comprised of one of: a wire, plastic, or ceramic mesh.

According to an embodiment, the device further comprises an in-situ analytical device positioned to analyze at least a portion of the collection well.

According to an embodiment, the in-situ analytical device is a Raman laser.

According to an embodiment, the particle focusing nozzle is narrower at the second end than at the first such that the gas-aerosol sample is accelerated out of the accelerator jet outlet.

According to an embodiment, the collection well is dimensioned and positioned such that the received gas-aerosol sample is subjected to at least two particle cut points.

According to an embodiment, the device further comprises an air flow generator.

According to another aspect, a method for collecting particulates from a gas-aerosol sample is provided. The method includes the steps of: providing an aerosol sampling device comprising a: a particle focusing nozzle comprising an elutriator column having an opening at a first end and an accelerator jet outlet at a second end opposite said first end, wherein the particle focusing nozzle is configured to receive a gas-aerosol sample at the opening and to vent the gas-aerosol sample at the jet outlet; a collection well, positioned to receive the gas-aerosol sample from the jet outlet, and comprising a backing and a sidewall, wherein at least a portion of the backing is porous such that at least part of the received gas-aerosol sample may flow through the porous portion of the backing; and a porous collection substrate in a covering relationship with the porous backing; inputting a gas-aerosol sample to the opening of the particle focusing nozzle; and analyzing a plurality of a particulates captured in the porous collection substrate.

According to an embodiment, the particulates are analyzed with an in-situ analytical device.

According to an embodiment, the in-situ analytical device is a Raman laser.

According to an embodiment, the collection well is suspended in a sampling chamber by a plurality of supports, wherein the supports are spaced to allow at least some of the gas received from the particle focusing nozzle to pass between the supports.

According to an embodiment, the porous portion of the backing is one of: a wire, plastic, or ceramic mesh.

These and other aspects of the invention will be apparent from the embodiments described below.

BRIEF DESCRIPTION OF THE DRAWINGS

The present invention will be more fully understood and appreciated by reading the following Detailed Description of the Invention in conjunction with the accompanying drawings in which:

FIG. 4 is a flowchart of a method for collecting particulates from a gas-aerosol sample in accordance with an embodiment.

DETAILED DESCRIPTION OF EMBODIMENTS

The present disclosure is directed to inventive methods and systems for an aerosol sampling device that can sample particulates while minimizing bounce and does not rely on the depth of the collection media to retain the particulates. Various embodiments and implementations herein are directed to a medium velocity aerosol sampling device that has a nozzle capable of focusing/concentrating the sampled particles by accelerating them in a narrow jet and driving the particles into an impaction well containing a collection substrate. The aerosolized particles, aerosolized droplets, and/or chemical vapors are retained by using a porous collection substrate, having substantial depth and mounted on a porous backing, such as a screen. This configuration allows a minor air flow through the collection substrate. This minor flow allows a well impactor to retain intercepted aerosolized particles. It also improves the inlet's ability to collect and retain chemical vapors or liquid aerosol droplets that are partially filtered and captured in the substrate's matrix.

Figure 1:
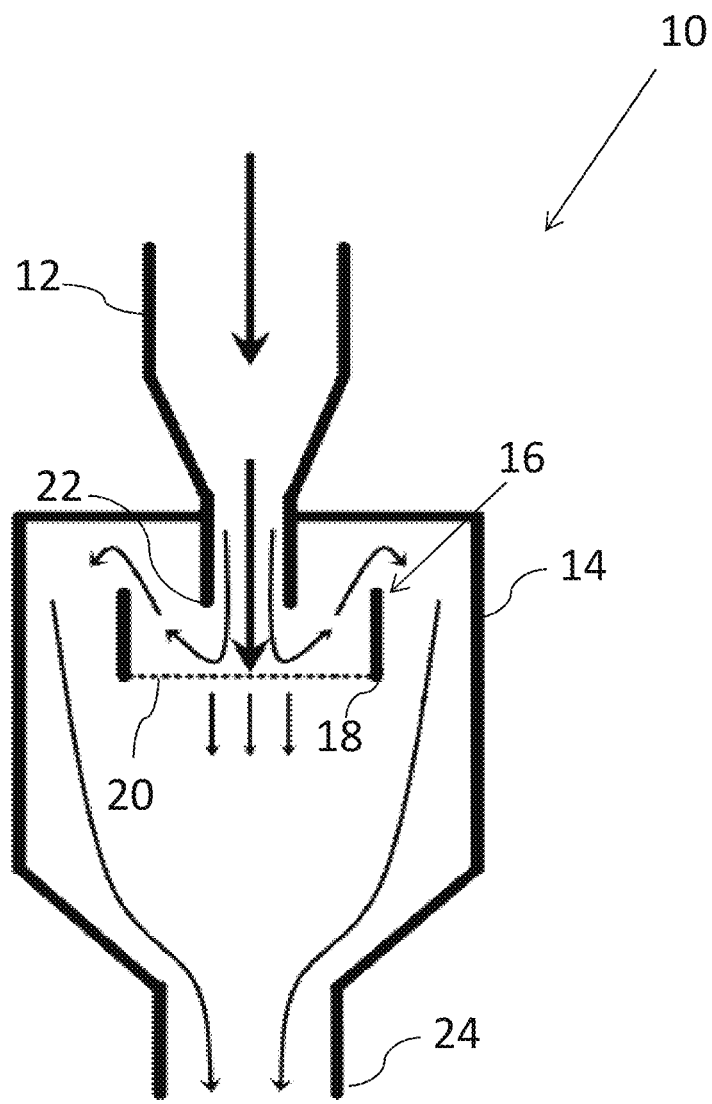
FIG. 1 is a schematic representation of an aerosol sampling method and device in accordance with an embodiment.

Referring now to the drawings wherein like reference numerals refer to like parts throughout, there is shown in FIG. 1 a schematic of an aerosol particulate capturing device 10. Device 10 includes a particle focusing nozzle 12 mounted on a sampling chamber 14 and positioned to deliver a gas-aerosol sample to a collection well 16 suspended within sampling chamber 14.

In an embodiment, collection well 16 may have at least one sidewall 18 and a backing 20. At least a portion of the backing 20 may be made of a porous material, such as wire, plastic, or ceramic mesh, such that the flow of gas may pass through the porous portion of backing 20. Collection well 16 may receive a porous collection substrate. The porous collection substrate may be arranged in a covering relationship with the porous portion of the backing 20, such that a minor flow of gas may permeate the porous collection substrate and porous portion of backing 20. In other words, a portion of the gas sample delivered to the collection well 16 will pass through the porous substrate and the porous portion of backing 20, depositing particulates within the porous collection substrate for later analysis. In alternate embodiments, the porous portion of collection well may be formed by slats, a lattice, or any other structural configuration that will allow gas to flow through backing 20.

Figure 2:
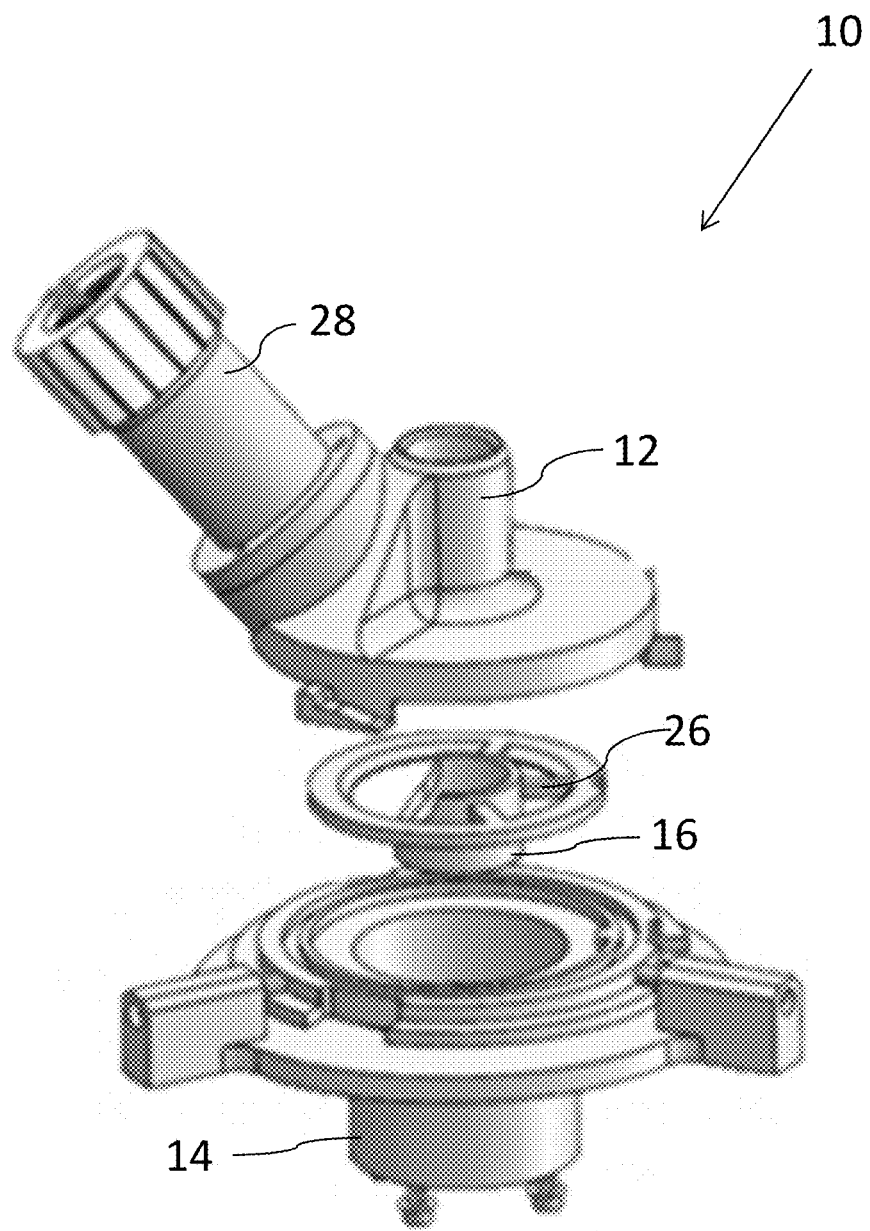
FIG. 2 is an exploded view of an aerosol sampling device in accordance with an embodiment.

As shown in FIG. 2, collection well 16 may be suspended within sampling chamber 14 by at least one support 26, spaced and positioned to allow a flow of gas between the supports 26. Thus, the portion of the gas-aerosol sample that does not flow through the porous collection substrate will travel up the sidewall 18 of collection well 16 and flow between supports 26, and out an outlet 24 of sampling chamber 14. In an embodiment, support 26 may be attached to ring that may, when device 10 is assembled, be seated within a bezel located at or near the first side of sampling chamber 14. Although supports are shown in FIG. 2 one of ordinary skill will appreciate that any porous support structure may be used, such that the gas-aerosol sample may flow out of collection well 16, and between collection well 16 and the walls of sampling chamber 14. For example, instead of individual supports, collection well 16 may be suspended with a wire, plastic, or ceramic mesh that ascends from the top cap of sampling chamber 14.

Returning to FIG. 1, in an embodiment, particle focusing nozzle 12 may have an opening to receive a gas-aerosol sample, and an accelerator jet outlet 22, at the opposite end, to vent the received gas-aerosol sample. In an embodiment, particle focusing nozzle narrows between the opening and the jet outlet 22 (i.e. in an embodiment, the jet outlet is narrower than the opening), in order to accelerate the gas-aerosol sample out of the jet outlet.

Sampling chamber 14, as shown, may have a first and second end. As described above, the first end is configured to receive particle focusing nozzle 12, and the second end has an outlet 24 configured to vent the received gas-aerosol sample. Like particle focusing nozzle, sampling chamber 14 may narrow at the second end so as to accelerate the flow of the remaining gas-aerosol sample out of outlet 24.

Figure 3A:
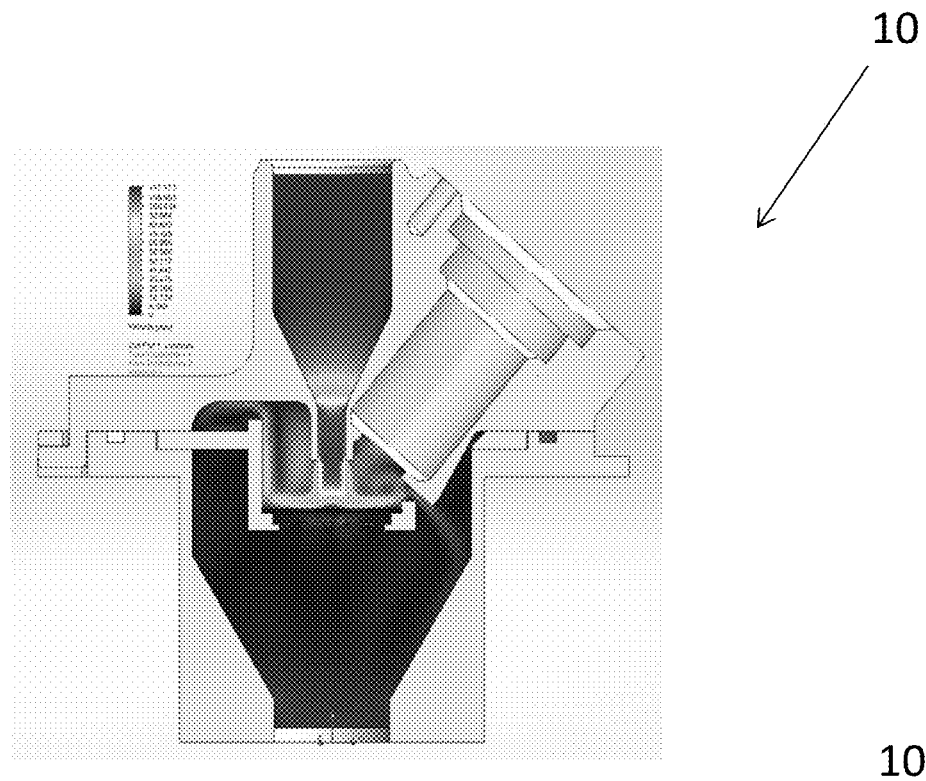
FIG. 3A is a simulated schematic representation of an aerosol sampling device during in accordance with an embodiment.
Figure 3B:
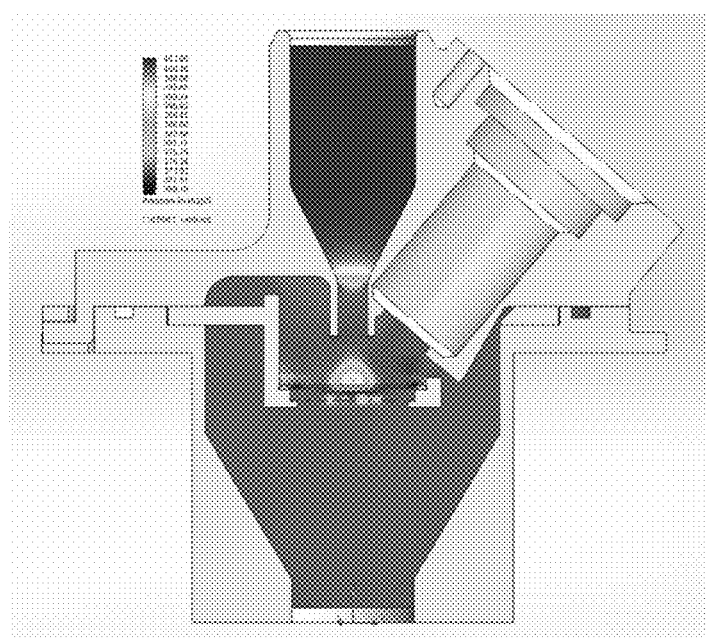
FIG. 3B is a simulated schematic representation of an aerosol sampling device during in accordance with an embodiment.

FIGS. 3A and 3B depict the velocity cut and pressure cut of device 10, during operation, respectively. Although device 10 is shown in various embodiments and figures as a single stage and particle cut-point, multiple stages and cut-points could be implemented to further separate and collect aerosolized particles of specific ranges of aerodynamic diameter, as will be appreciated by a person of skill in the art. This could be accomplished by adjusting a number of parameters in the sampling device. Such parameters include the ratio of well diameter to the jet diameter, the well/well wall height to jet distance, or well wall to outlet wall distance. Additional parameters include the porosity, pore size, and thickness of the porous collection substrate that could be adjusted to further separate and collect aerosolized particles of specific ranges of aerodynamic diameter, plus change the portion of the gas-aerosol sample passing through the substrate and the porous portion of backing 20 affecting aerosol capture efficiency. As will be appreciated by a person of ordinary skill, each of these design parameters, in addition to the sampling flow, affect the aerosol cut-point of the aerosol sampling device 10.

FIG. 3B displays the pressure drop formed across the porous collection substrate and the porous portion of backing 20 resulting in flow of a portion of the gas-aerosol sample through the porous collection substrate trapping aerosol particles, aerosol droplets, and chemical vapors within the porous collection substrate matrix. As will be appreciated by a person of ordinary skill, each of the design parameters discussed above, in addition to the sampling flow, affect the chemical vapor capture efficiency of the aerosol sampling device 10.

Returning to FIG. 2, device 10 may further include an in-situ analytical device, such as laser 28 positioned to illuminate the collection well, such that the captured particulates may be analyzed. In an embodiment, sampling laser 28 may be a Raman laser, although other suitable lasers or other analytic devices may be employed in alternate embodiments.

Device 10 may further include an air flow generating device, such as a fan, blower, or vacuum pump. Device 10 may operate under DC or AC power for continuous indoor building aerosol monitoring, remote outdoor sampling, or clandestine field applications. The filter may be analyzed in place by spectroscopic methods, removed from the collection well 16 and interfaced with other analytical instrumentation such as LC-MS, GC-MS, TGA, ICP, ICP/MS, FAA, or GFAA.

Alternate and additional embodiments may include a rain shield or noise dampening muffler.

FIG. 4 depicts a flowchart of a method 500 for collecting particulates from a gas-aerosol aerosol sample. In step 502, aerosol sampling device 10, as described above in various embodiments, is provided. In particular, aerosol sampling device 10 has a collection well with a porous backing that is configured to receive a porous collection substrate, such that a portion of any gas admitted to the sampling chamber may pass through the porous collection substrate and through the porous portion of the backing. In step 504, a gas sample that contains a plurality of particulates to be analyzed is inputted to the system. In step 506, the particulates that are captured in the collection substrate are analyzed. In an embodiment, the captured particulates may be analyzed with a laser, such as a Raman laser, that is positioned to illuminate the collection substrate.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. An aerosol and vapor sampling device, comprising:
    a sampling chamber comprising an inlet and an outlet and comprising an inner surface defining an inner volume;
    a particle focusing nozzle comprising an elutriator column having an opening at a first end and an accelerator jet outlet at a second end opposite said first end, wherein the particle focusing nozzle is configured to admit a gas-aerosol sample at the opening and to vent the gas-aerosol sample into the sampling chamber via the jet outlet; and
    a collection well positioned within the sample chamber to receive a portion of the gas-aerosol sample from the jet outlet, the collection well comprising a backing and a sidewall, wherein at least a portion of the backing is porous such that at least part of the received gas-aerosol sample may flow through the porous portion of the backing;
    wherein the collection well is suspended approximately in the center of the inner volume of the sample chamber to define a gap between the sidewall of the collection wall and the inner surface of the sampling chamber;
    wherein only a portion of the gas-aerosol sample from the particle focusing nozzle, being less than all of the gas-aerosol sample, enters the collection well, and the remainder of the gas-aerosol sample from the particle focusing nozzle enters the gap between the sidewall of the collection wall and the inner surface of the sampling chamber.

2. The device of claim 1, further comprising a porous collection substrate in a covering relationship with the porous backing such that at least a portion of the gas-aerosol sample passes through the porous collection substrate.

3. The device of claim 1, wherein the collection well is suspended in the sampling chamber by a plurality of supports, wherein the supports are spaced to allow at least some of the gas received from the particle focusing nozzle to pass between the supports and to exit the sampling chamber via the second end.

4. The device of claim 1, wherein the porous portion of the backing is comprised of one of: a wire, plastic, or ceramic mesh.

5. The device of claim 1, further comprising an in-situ analytical device positioned to analyze at least a portion of the collection well.

6. The device of claim 5, wherein the in-situ analytical device is a Raman laser.

7. The device of claim 1, wherein the particle focusing nozzle is narrower at the second end than at the first such that the gas-aerosol sample is accelerated out of the accelerator jet outlet.

8. The device of claim 1, wherein the collection well is dimensioned and positioned such that the received gas-aerosol sample is subjected to at least two particle cut points.

9. The device of claim 1, further comprising an air flow generator.

10. A method for collecting particulates and vapors from a gas-aerosol sample, comprising the steps of:
   providing an aerosol sampling device comprising: (i) a sampling chamber comprising an inlet and an outlet and comprising an inner surface defining an inner volume; (ii) a particle focusing nozzle comprising an elutriator column having an opening at a first end and an accelerator jet outlet at a second end opposite said first end, wherein the particle focusing nozzle is configured to receive a gas-aerosol sample at the opening and to vent the gas-aerosol sample into the sampling chamber via the jet outlet; (iii) a collection well positioned within the sample chamber to receive a portion of the gas-aerosol sample from the jet outlet, the collection well comprising a backing and a sidewall, wherein at least a portion of the backing is porous such that at least part of the received gas-aerosol sample may flow through the porous portion of the backing; and (iv) a porous collection substrate in a covering relationship with the porous backing, wherein the collection well is suspended approximately in the center of the inner volume of the sample chamber to define a gap between the sidewall of the collection wall and the inner surface of the sampling chamber; and further wherein only a portion of the gas-aerosol sample from the particle focusing nozzle, being less than all of the gas-aerosol sample, enters the collection well, and the remainder of the gas-aerosol sample from the particle focusing nozzle enters the gap between the sidewall of the collection wall and the inner surface of the sampling chamber;
   inputting a gas sample to the opening of the particle focusing nozzle; and
   analyzing a plurality of a particulates, droplets, and/or vapors captured in the porous collection substrate.

11. The method of claim 10, wherein the particulates are analyzed with an in-situ analytical device.

12. The method of claim 11, wherein the in-situ analytical device is a Raman laser.

13. The method of claim 10, wherein the collection well is suspended in a sampling chamber by a plurality of supports, wherein the supports are spaced to allow at least some of the gas received from the particle focusing nozzle to pass between the supports.

14. The method of claim 10, wherein the porous portion of the backing is one of: a wire, plastic, or ceramic mesh.

* * * * *